United States Patent [19]
Williams et al.

[11] Patent Number: 5,331,968
[45] Date of Patent: Jul. 26, 1994

[54] INDUCTIVE PLETHYSMOGRAPHIC TRANSDUCERS AND ELECTRONIC CIRCUITRY THEREFOR

[76] Inventors: Gerald Williams, 485 Ridgewood Rd., Key Biscayne, Fla. 33149; Herman Watson, 105 11 S.W. 12 Ct., Miami, Fla. 33186; Marvin A. Sackner, 300 Rivo Alto Dr., Miami Beach, Fla. 33139; Chu Pak, 6525 Chapman Field Dr., Miami, Fla. 33156; James W. Chong, 10650 S.W. 69th Ave., Miami, Fla. 33156

[21] Appl. No.: 32,835
[22] Filed: Mar. 10, 1993

Related U.S. Application Data

[63] Continuation of Ser. No. 601,168, Oct. 19, 1990, abandoned.

[51] Int. Cl.5 .................................................. A61B 5/02
[52] U.S. Cl. ..................................... 128/721; 128/722
[58] Field of Search ............... 128/734, 721, 722, 716, 128/719, 670, 671

[56] References Cited

U.S. PATENT DOCUMENTS

| | | |
|---|---|---|
| 3,731,184 | 5/1973 | Goldberg . |
| 4,308,872 | 1/1982 | Watson et al. . |
| 4,373,534 | 2/1983 | Watson ................................ 128/721 |
| 4,433,693 | 2/1984 | Hochstein .......................... 128/721 |
| 4,452,252 | 6/1984 | Sackner ............................... 128/671 |
| 4,494,553 | 1/1985 | Sciarra ................................ 128/671 |
| 4,807,640 | 2/1989 | Watson . |
| 4,815,473 | 3/1989 | Watson et al. ..................... 128/721 |
| 4,817,625 | 4/1989 | Miles .................................. 128/721 |
| 4,834,109 | 5/1989 | Watson . |

FOREIGN PATENT DOCUMENTS 2116725 9/1983 United Kingdom ................ 128/721

OTHER PUBLICATIONS

Respiratory inductance plethysmography with an electrical impedance plethysmograph, Sinton and Suntheratingam, Medical & Biological Engineering & Computing, Mar. 1988, pp. 213-217.

*Primary Examiner*—Lee S. Cohen
*Assistant Examiner*—Robert L. Nasser, Jr.
*Attorney, Agent, or Firm*—Cohen, Pontani, Lieberman, Pavane

[57] ABSTRACT

The present invention is an apparatus and method for improving the detection of the inductance "signal" generated by an inductive plethysmograph (12). Signal detection is improved by modifying the design of the inductive plethysmograph (12) and also by improving the design of the associated circuitry. By virtue of these improvements, the associated circuitry may be located remotely rather than on the transducer, as is the current practice. In one aspect of the invention, the impedance matching transformer (14) joining the inductive plethysmograph (12) to the oscillator (16) is selected such that the inductance of its primary winding is greater than about ten times the reflected inductance of the inductive plethysmograph (12) and the cable (24) joining it to the transformer (14). In accordance with another aspect of the invention, the inductive plethysmograph (12) is modified such that the conductor (20) incorporated therein encircles the relevant body portion a plurality of times. In yet a further aspect of the invention, the cable (24) connecting the inductive plethysmograph (12) to the transformer (14) is selected such that the ratio of the diameter of its screen to the diameter of its center conductor is minimized for reducing the inductance per unit length thereof.

31 Claims, 3 Drawing Sheets

INDUCTIVE PLETHYSMOGRAPHIC TRANSDUCERS AND ELECTRONIC CIRCUITRY THEREFOR

This is a continuation of U.S. application Ser. No. 07/601,168, filed Oct. 19, 1990, now abandoned.

BACKGROUND OF THE INVENTION

1. Field of the Invention

This invention pertains to inductive plethysmographic transducers of the type used in apparatus for monitoring body functions, such as respiration and heart volumes. More particularly, the present invention pertains to improvements in the design of such transducers and the electronic circuitry associated therewith.

2. State of the Prior Art

Commonly assigned U.S. Pat. No. 4,308,872 entitled METHOD AND APPARATUS FOR MONITORING RESPIRATION, the contents of which are incorporated herein by reference, discloses a particular respiration monitoring apparatus. The apparatus disclosed in the patent employs two electrical conductors, e.g., wires, one disposed in encircling relation about the chest and the other disposed in encircling relation about the abdomen. Each conductor comprises the inductance element of an LC oscillator circuit of fixed capacitance. Consequently, the frequency of each oscillator varies solely in response to changes in the inductance of its respective conductor which, in turn, varies in response to changes in the cross-sectional area encircled by the conductor. Therefore, in the case of respiratory applications, as the subject breathes the frequency changes at the outputs of the oscillators continuously indicate the extent of expansion and contraction of the subject's chest and abdomen. As more fully explained in said U.S. Pat. No. 4,308,872, by appropriate processing and calibration of these signals, significant respiration data may be obtained. In the art, each of the conductors and their supporting structure is referred to as an inductive plethysmograph. The assignee hereof markets such inductive plethysmographs under the trademark Respiband ™.

As noted, each inductive plethysmograph requires an LC oscillator and associated circuitry. As presently marketed by the assignee hereof, the LC oscillator and its associated circuitry are housed in a plastic module removably secured to the inductive plethysmograph. Wires extending from the module connect the oscillator circuitry with a remote housing containing circuitry for processing, calibrating and displaying, the frequency changes detected by the oscillator and for displaying the results. Typically, the length of the cable connecting the oscillator module on an inductive plethysmograph with the remote housing is about ten feet. The oscillator module as well as an improved inductive plethysmograph are disclosed in commonly assigned U.S. Pat. No. 4,807,640 entitled STRETCHABLE BAND-TYPE TRANSDUCER PARTICULARLY SUITED FOR RESPIRATION MONITORING APPARATUS, the contents of which are incorporated herein by reference.

Although the arrangement of U.S. Pat. No. 4,807,640 represents an improvement over the prior art, particularly insofar as the oscillator circuitry is simplified and the system is rendered more convenient to use, it too is not without drawbacks. For example, it has been observed that untrained personnel often damage the oscillator modules by pulling vigorously on their wire leads. Moreover, when applied to infants and newborns, even the smallest oscillator modules are inordinately bulky and potentially uncomfortable, as when the infant or newborn is lying thereon.

The ideal solution would be simply to move the oscillator circuitry to the remote housing, with the inductive plethysmograph connected to the oscillator circuitry by a wire cable. Unfortunately, this results in a substantial loss of signal, typically about 90%. In this regard, it will be recalled that the electronic parameter which forms the basis for all measurements is the change in the inductance of the inductive plethysmograph. A typical inductive plethysmograph has an inductance of only one to two microhenries, and obviously the changes being detected are substantially less than that. However, a ten foot length of standard coaxial cable, which is approximately the length of cable that would be required to connect the inductive plethysmograph to the remotely housed oscillator circuit, typically has an inductance of several times the inductance of the inductive plethysmograph. As the inductance of the wire cable is in series with the inductance of the inductive plethysmograph, it will be apparent that with a remotely housed oscillator circuit, changes in the inductance of the inductive plethysmograph will represent a relatively small percentage change in the combined inductances of the inductive plethysmograph and wire cable. This is to be contrasted with the situation where such inductive changes are measured relative to the inductance of the inductive plethysmograph alone, as is the case in the arrangement disclosed in U.S. Pat. No. 4,807,640, wherein the oscillator circuit is secured directly to the inductive plethysmograph.

It is accordingly an object of the present invention to provide an improved system comprising an inductive plethysmograph and oscillator circuit therefor wherein the oscillator circuit may be housed remotely from the inductive plethysmograph without a substantial signal loss.

It is a further object of the invention to provide a system wherein the oscillator circuitry may be housed remotely from the inductive plethysmograph and signal loss is reduced by improving the circuit design.

It is yet a further object of the invention to provide a system wherein the oscillator circuit may be housed remotely from the inductive plethysmograph and signal loss is reduced by improving the design of the inductive plethysmograph itself.

DISCLOSURE OF THE INVENTION

The present invention is intended for incorporation in an apparatus of the type comprising at least one inductive plethysmograph incorporating a conductor, the conductor comprising the inductance component of an LC oscillator circuit, with the conductor being connected to the oscillator through an impedance matching transformer having its secondary winding connected to the conductor and its primary winding connected to the oscillator circuit. In such an apparatus, the improvement of the present invention, broadly speaking, comprises the oscillator and transformer being disposed remotely from the inductive plethysmograph with the conductor incorporated in the inductive plethysmograph being joined to the transformer via a connecting cable, and the transformer having a primary winding whose inductance is greater than about ten times the reflected inductance of the conductor and the cable. By virtue of this improvement, attenuation of changes in the inductance of the conductor is reduced, with the consequence that a stronger inductance "signal" is detected at the oscillator circuit. A method implementing this improvement is also disclosed.

In a further improvement in accordance with the present invention intended for incorporation in an apparatus of the type comprising at least one inductive plethysmograph incorporating a conductor adapted for placement in encircling relation about a body portion of a subject, the conductor comprising the inductance component of an LC oscillator circuit, the improvement comprises the conductor having a plurality of turns such that when the inductive plethysmograph is in encircling relation about the body portion, the conductor encircles the body portion a plurality of times for improving the sensitivity of the apparatus to changes in the inductance of the conductor. In a preferred embodiment of this improvement, the inductive plethysmograph comprises a stretchable substrate on which the conductor is arranged in a zigzag pattern, and the inductive plethysmograph has two free ends joinable by mating connectors with the conductor comprising individual lengths of wire supported on the substrate with one end of each conductor being joined to one of the mating connectors and the other end being joined to the other of the mating connectors, whereby when the connectors are joined, a conductor having a plurality of turns is formed. A method for implementing this improvement is also disclosed.

In accordance with yet a further improvement of the present invention intended for incorporation in an apparatus of the type comprising at least one inductive plethysmograph incorporating a conductor which comprises the inductive component of an LC oscillator circuit, the conductor being connected to the oscillator circuit through an impedance matching transformer having its secondary winding connected to the conductor and its primary winding thereof connected to the oscillator circuit, the improvement comprises the oscillator circuit and the transformer being disposed remotely from the conductor and joined thereto by a coaxial cable, the ratio of the diameter of the screen of the cable to the diameter of its center conductor being minimized for reducing the inductance per unit length thereof, whereby the sensitivity of the apparatus to changes in the inductance of the conductor in the inductive plethysmography is further improved. In accordance with a preferred embodiment of this improvement, the coaxial cable has an inductance of about 0.03 microhenries per foot.

Further features and advantages of the apparatus and methods in accordance with the present invention will be more fully apparent from the following detailed description and annexed drawings of the presently preferred embodiments thereof.

DETAILED DESCRIPTION OF THE PREFERRED EMBODIMENT

Figure 1:
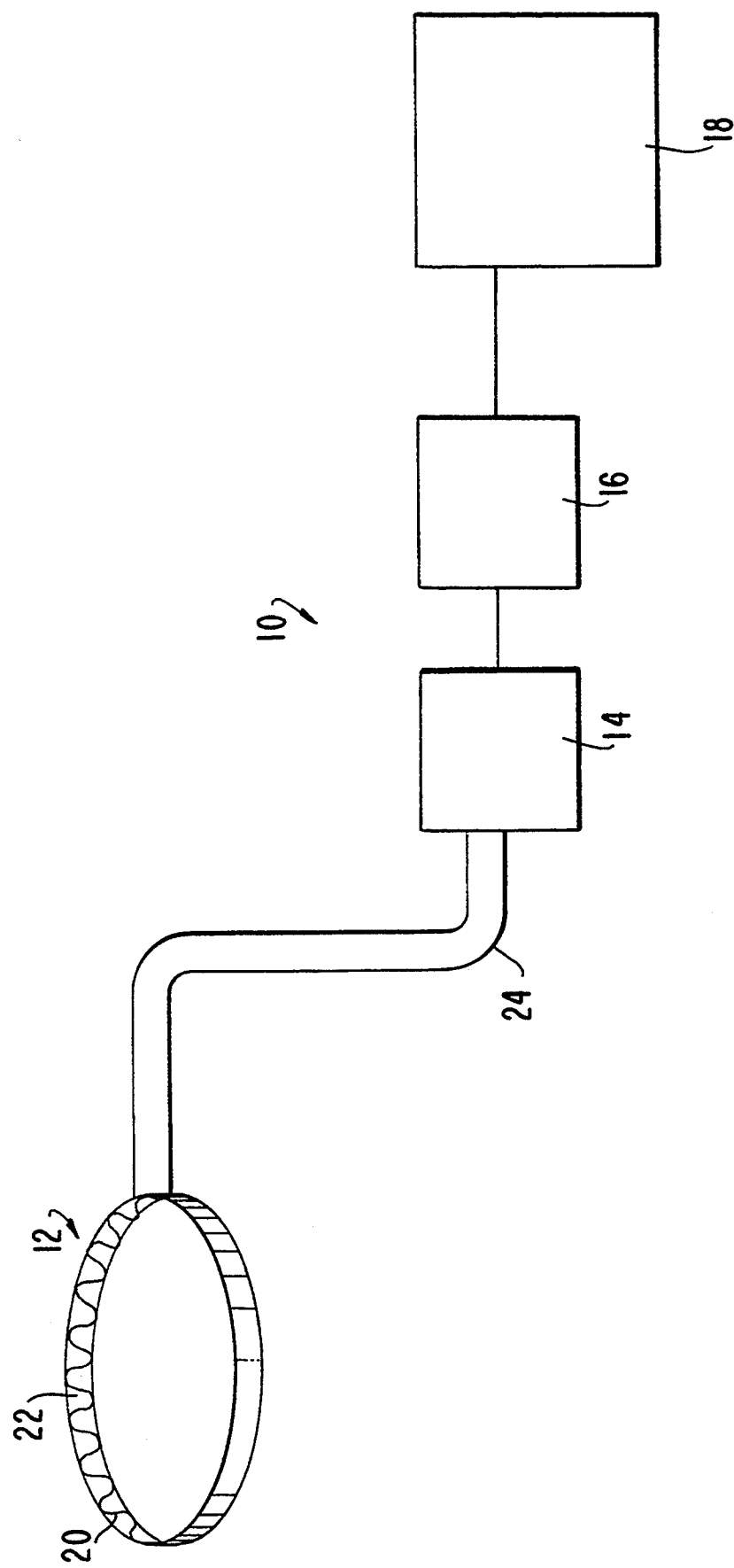
FIG. 1 is a diagrammatic representation of a system incorporating the present invention.

Referring now to the drawings, and initially to FIG. 1, the present invention is employed in connection with a system of the type generally designated by the reference numeral 10. As shown, the system 10 includes an inductive plethysmograph 12, an impedance matching transformer 14, an LC oscillator circuit 16 and a calibration and measurement apparatus 18. As is well known in the art, the inductive plethysmograph 12 comprises a wire conductor 20 supported on a stretchable substrate 22 dimensioned for a close fit about the torso of a subject. For a more detailed discussion of the possible constructions of the inductive plethysmograph 12, the reader is referred to commonly owned U.S. Pat. Nos. 4,308,872 and 4,807,640, the contents of which are incorporated herein by reference in their entireties.

Where the inductive plethysmograph 12 is used, for example, for monitoring respiration, changes in the subject's torso dimension result in expansion and contraction of the substrate 22 and corresponding changes in the shape of the conductor 20. Changes in the shape of the wire conductor 20 result, in turn, in changes in its inductance, and it is these inductance changes which are measured by the system 10 as more fully described in the aforementioned commonly assigned U.S. Pat. No. 4,308,872. It has been found, for example, that the measured changes in inductance, after appropriate calibration, reflect changes in the subject's respiration volume, such that the system 10 is capable of recording and measuring a variety of respiration parameters, including tidal volume. Cardiac functions may also be detected and measured with the system 10 as more fully described in commonly owned application Ser. No. 326,159, the contents of which are incorporated herein by reference in their entirety.

In respiratory applications, the system 10 includes two inductive plethysmographs 12, each having its own impedance matching transformer 14 and oscillator circuit 16, one band being disposed about the subject's chest and the other about the abdomen. However, for the sake of simplicity, only one of the inductive plethysmographs 12 is shown in FIG. 1.

As noted earlier, the inductance of the wire conductor 20 of the inductive plethysmograph 12 is measured by incorporating the wire conductor 20 as the inductance element of an LC oscillator circuit 16, such that changes in the inductance of the wire conductor 20 resulting from changes in the shape thereof are reflected as corresponding changes int he frequency of the oscillator, with such frequency changes being calibrated and measured by the apparatus 18. Suitable apparatus 18 for calibrating and measuring the frequency changes of the oscillator circuit 16 are more fully described in the aforementioned commonly assigned U.S. Pat. No. 4,308,872, as well as in commonly assigned U.S. Pat. No. 4,834,109, the contents of which are incorporated herein by reference in their entireties. A commercial system for performing this operation is also available from the assignee hereof, Non-Invasive Monitoring Systems, Inc., and is sold under the trade name Respigraph TM. However, a detailed understanding of the apparatus 18 is not necessary for an understanding of the present invention.

Still referring to FIG. 1, the matching transformer 14 is required to match the impedance of the wire conductor 20 of the inductive plethysmograph 12 to the oscillator circuit 16. The presently preferred input impedance to the oscillator circuit 16 is 150 ohms, which is considerably higher than the low impedance of the wire conductor 20. Actually, the input impedance to the matching transformer 14 comprises the impedance of the wire conductor 20 in series with the cable 24 which connects the conductor 20 to the transformer 14. As mentioned earlier, in practice the length of the cable 24 is about 10 feet. However, and as will be apparent to persons of ordinary skill in the art, the combined impedance of the conductor 20 and cable 24 is still considerably below the 150 ohms input impedance required at the oscillator circuit 16.

For the system 10 to be accurate, it will be apparent that changes in the inductance of the wire conductor 20 must be reflected, with minimum loss, as changes in the inductance element of the oscillator circuit 16. As inductance changes in the conductor 20 are transmitted to the oscillator circuit 16 via transformer 14, the present inventors recognized the importance of avoiding inductance losses at the transformer. Accordingly, an investigation was undertaken to determine the nature of such losses with the ultimate goal of minimizing them. Proper design of the transformer 14 is particularly critical since the "signal" to be measured is an inductance change, as opposed to the typical situation wherein the signal is a voltage level.

Figure 2:
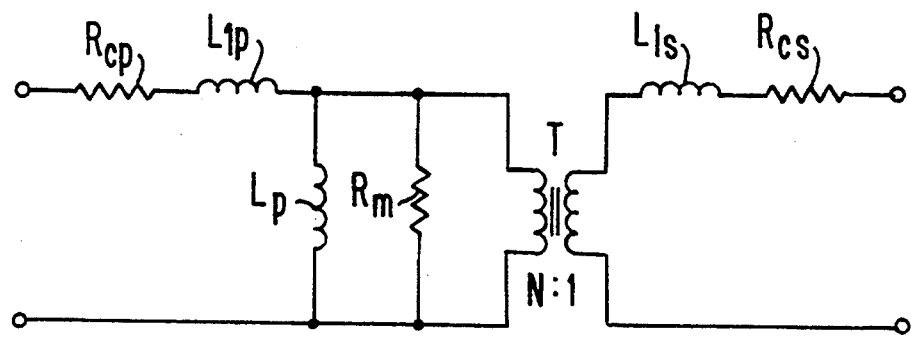
FIG. 2 is a schematic representation of an equivalent circuit for a transformer of the type used in the present invention.

Referring now to FIG. 2, an equivalent circuit for a small, ferrite core transformer of the type employed in the system 10 is generally designated by the reference numeral 26. As shown, the oscillator circuit 16 is connected to the primary winding of the transformer 26 and the wire conductor 20 is connected to the secondary winding. Actually, and as shown in FIG. 1, the conductor 20 is connected to the secondary winding via the cable 24. In FIG. 2, T represents an ideal transformer of turns ratio N. $R_{cp}$ and $R_{cs}$ represent, respectively, the copper losses of the primary and secondary windings, and $R_m$ represents the magnetic losses in the core. $L_p$ represents the inductance of the primary with the secondary winding open-circuited. As is known in the art, the value of $L_p$ is a function of the type of ferrite material employed in the core as well as the size of the core, with $L_p$ being proportional to the square of the number of turns in the primary winding. $L_{lp}$ and $L_{ts}$ represent the leakage inductances of the primary and secondary which arise because magnetic coupling between the primary and secondary is never perfect, i.e., some of the flux at the primary "leaks" out of the core without linking the secondary, and vice-versa.

Figure 3:
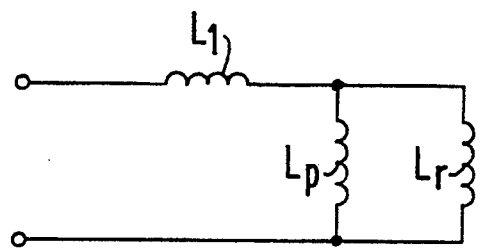
FIG. 3 is a simplified schematic representation of the transformer of FIG. 1.

In the system 10, core losses are low with the consequence that $R_m$ is on the order of about 1 megaohm, which can be neglected in comparison with other circuit impedances. The copper losses $R_{cp}$ and $R_{cs}$ are also insignificant. Consequently, if all inductances are reflected into the primary, the result is the simplified equivalent circuit shown in FIG. 3. In FIG. 3, the inductance of the secondary winding, being sufficiently large, has been ignored. In the simplified equivalent circuit of FIG. 3, $L_1$ represents the leakage inductances of the primary and secondary and is equal to $L_{lp}+(L_{ls}\cdot N^2)$, and $L_r$ represents the reflected inductances of the conductor 20 and cable 24 and is equal to $N^2\cdot(L_b+L_c)$, where $L_b$ is equal to the inductance of the conductor 20 and $L_c$ is equal to the inductance of the cable 24.

Measurements conducted with the secondary winding short-circuited show that the total leakage inductance of the transformer 14 is about one (1%) percent of the inductance of the primary winding $L_p$ over a wide range of primary inductances and turns ratios. With this in mind, it will be apparent from the simplified equivalent circuit of FIG. 3 that the inductance of the primary $L_p$ must be properly selected to prevent distortion of the actual inductance changes in the conductor 20. That is, if the inductance of the primary $L_p$ is too small, it will be apparent from the circuit of FIG. 3 that $L_p$ will shunt changes in the inductance of the conductor 20. Conversely, if $L_p$ is too large the correspondingly large leakage inductance $L_l$ which, as noted above, is approximately one (1%) percent of the primary inductance Lp, will attenuate changes in the inductance of the conductor 20 by adding a series inductance component to $L_r$. This suggests, and empirical studies confirm, that an optimum value for $L_p$ is approximately 10 times the reflected inductance of the conductor 20 and cable 24, $L_r$.

Based on the foregoing discussion, the design parameters for the transformer 14 are now defined. Initially, the turns ratio is selected such that the combined impedance of the conductor 20 and cable 24 is stepped up to 150 ohms to match the input impedance for the oscillator circuit 16. Next, the primary inductance $L_p$ is selected, as by using manufacturer's spec sheets, to be about ten (10) times $L_r$, the reflected inductance of the conductor 20 and cable 24. That is, $L_p$ is selected such that:

$$L_p = 10 \cdot N^2 \cdot (L_b + L_c) \tag{Eq. 1}$$

It will be recalled that the factor 10 is derived from the typical 100:1 ratio of the primary inductance $L_p$ to the reflected leakage inductance $L_l$ characteristic of a wide range of available transformers. However, certain transformers display different ratios of $L_p$ to $L_1$. For example, for toroidal transformers, the ratio is higher than 100:1, and consequently the ratio of the primary inductance $L_p$ to $L_r$, the reflected inductance of the conductor 20 and band 24, is correspondingly greater than 10.

Turning now to a second aspect of the present invention, as noted in the Prior Art section of this application, moving the oscillator circuit 16 to a location remote from the inductive plethysmograph 12 necessarily requires the use of a cable 24, with a resulting loss of signal. Again, it must be remembered that the "signal" of interest here is inductance changes in the conductor 20. The cable 24, which is typically a coaxial cable at least 10 feet long, has an inductance several times that of the 1-2 microhenries of the conductor 20. Consequently, changes in the inductance of the conductor 20 must now be detected relative to the summed inductances of the cable 24 and conductor 20, as contrasted with the situation when the oscillator circuit 16 is adjacent the inductive plethysmograph, in which case the changes in inductance are detected only relative to the inductance of the conductor 20 itself.

It was determined, therefore, that the adverse impact of introducing the cable 24 can be reduced by minimizing the inductance of the cable. Reference texts, such as Bleaney, B. I. and Bleaney, B., *Electricity and Magnetism,* Oxford University Press, First Ed., 1957, establish that a major factor contributing to the inductance of a coaxial cable is the ratio of the diameter of the outer screen to the diameter of the central conductor. In particular, if the ratio is large, i.e., large diameter screen, small diameter conductor, the cable has a large inductance and a relatively small capacitance per unit length. For the present application, of course, the cable 24 should be selected such that it has a minimum inductance per unit length, at least less than about 0.1 microhenries per foot. Consequently, the ratio of the diameter of the screen to the conductor should be selected to be as small as possible. A preferred cable 24 for use with the present invention is #10087 manufactured by Minnesota Wire & Cable, Inc., 1835 Energy Park Drive, St. Paul, Minn. 55108 which has the desired low ratio as well as other desirable mechanical properties, such as flexibility and small overall diameter. This cable 24 has a measured inductance of about 0.3 microhenries per 10 foot length or about 0.03 microhenries per foot. The correspondingly large capacitance of about 410 picofarads for this cable does not present a problem for the LC oscillator circuit 16, as it is swamped by the substantially larger 0.1 microfarad capacitor required to tune the oscillator circuit 16 for resonance at its operating frequency of about 250 kHz.

We have found that by properly selecting the cable 24 and designing the transformer circuit 14 in accordance with the disclosure set forth hereinabove, the oscillator circuit 14 can be moved to a location up to 10 feet remote from the inductive plethysmograph 12 while keeping the signal loss to less than ten (10%) percent as compared with the prior art arrangement wherein the oscillator circuit 16 is in a module secured directly to the inductive plethysmograph. As would be expected, increasing the distance beyond 10 feet results in a slightly greater signal loss due primarily to the concomitant increase in the inductance of the cable 24. For reasons already noted hereinabove, it is highly desirable to move the oscillator circuit 16 to a location remote from the subject, especially in the case of infants and newborns. Accordingly, the present invention has a substantial practical application.

Thus far, improving the signal from the inductive plethysmograph has focused on reducing the inductance of the connecting cable 24 and improving the circuit design of the impedance matching transformer 14. As is now more fully described below in connection with FIGS. 4 and 5, the signal from the inductive plethysmograph 12 available at the calibrating and measurement apparatus 18 may be further improved by modifying the design of the inductive plethysmograph 12.

Inductive plethysmographs now in use utilize a single turn of wire, typically in a zigzag pattern, supported on a stretchable substrate. See, for example, the inductive plethysmograph disclosed in commonly owned U.S. Pat. No. 4,807,640. While such an arrangement is convenient from a practical point of view (manufacturing ease, reduced production cost, etc.) and produces a signal which is adequate for respiratory applications wherein the movements being detected are relatively pronounced, there is a demand for greater sensitivity when the inductive plethysmograph is used for measuring less pronounced movements, such as those due to changes in heart volume as measured during thoracocardiography.

Figure 4:
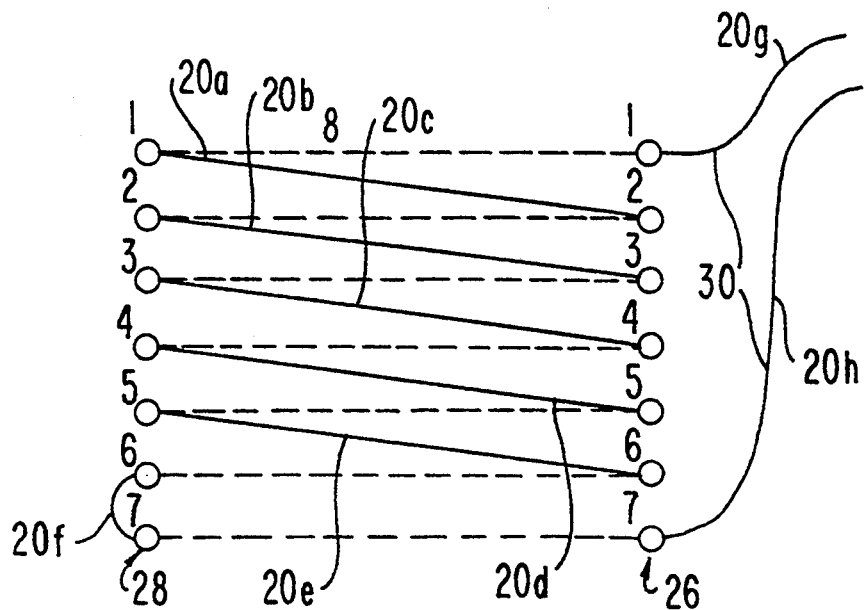
FIG. 4 is a diagrammatic representation of an improved wiring arrangement for an inductive plethysmograph in accordance with the present invention.
Figure 5:
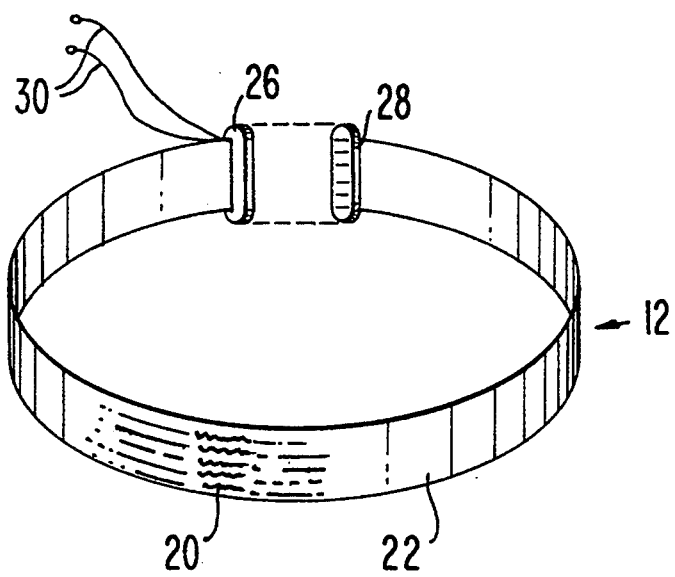
FIG. 5 is a perspective representation of an improved inductive plethysmograph in accordance with the present invention.

In accordance with the present invention, we have found that the sensitivity of the inductive plethysmograph may be increased by incorporating multiple turns of wire, rather than a single turn. One approach to construction of a multiple-turn inductive plethysmograph is illustrated in FIGS. 4–5. As best shown in FIG. 5, the improved inductive plethysmograph comprises a single conductor 20 arranged in multiple turns on a stretchable substrate 22. The method of securing the wire 20 on the substrate 22 and the composition of the substrate may be as disclosed in commonly assigned U.S. Pat. Nos. 4,308,872 and 4,807,640. As shown in FIG. 5, the two ends of the inductive plethysmograph 12 are joined by mating male and female multi-pin connectors 26 and 28, respectively, with the free ends 30 of the conductor 20 protruding from the female connector 26 though, as will be apparent hereinafter, they could just as well protrude from the male connector 28.

In the embodiment illustrated in FIGS. 4–5, the inductive plethysmograph 12 comprises a conductor 20 having five turns. That is, when the inductive plethysmograph 12 is placed about the torso or other body part of a subject, with the connectors 26 and 28 joined, the conductor encircles the torso five times. The use of connectors 26 and 28 is preferred as this facilitates placement of the inductive plethysmograph on the subject. However, constructions dispensing with connectors 26 and 28 will be apparent to those of ordinary skill in the art once this description is known.

FIG. 4 shows the manner in which the conductor 20 is joined to the female and male connectors 26 and 28, respectively. In FIG. 4, the dotted lines indicate connections made by joining the connectors 26, 28, and solid lines represent the lengths of wire supported on the substrate 22. From FIG. 4, it will be apparent that the conductor 20 actually comprises five separate lengths of wire $20a$–$20e$ and a jumper $20f$, such that when the mating halves of the connectors 26, 28 are joined, a single, multiple-turn conductor 20 is formed having free ends 30. As shown, the free ends 30 of the wire comprise additional short lengths of wire $20g$ and $20h$ connected, respectively, to pins 1 and 7 of the female conductor 26. It is contemplated that the free ends of these wires $20g$ and $20h$ will be joined to a coaxial connector which, in turn, will mate with one end of the cable 24 joining the inductive plethysmograph 12 to the transformer 14 (see FIG. 1).

The improved sensitivity of the inductive plethysmograph 12 of FIGS. 4 and 5 as compared with a single-turn inductive plethysmograph in accordance with the prior art results from an improved signal-to-noise ratio and a larger absolute signal. Regarding the signal-to-noise ratio, the efficiency of a tuned circuit, such as the oscillator circuit 16 of FIG. 1, is typically stated as a Q-factor. The Q-factor is proportional to the ratio of the inductance in the circuit divided by the circuit's electrical losses, such as wire resistances, eddy current losses, etc. The inductance of a wire coil, such as the wire conductor 20 in the inductive plethysmograph 12, varies as the square of the number of turns in the coil, in this case five turns, while the losses generally increase linearly with the number of turns. Consequently, it can be seen that the Q-factor of a tuned circuit incorporating a wire coil will also increase with the number of turns. When the tuned circuit comprises part of an oscillator, the stability of the oscillator frequency, and hence the minimum frequency change that can be detected, is a direct function of the Q-factor, i.e. the higher the Q-factor, the lower the frequency jitter. In the case of the inductive plethysmograph, a reduced frequency jitter results in an improved signal-to-noise ratio, thereby increasing the sensitivity of the device.

Regarding the increase in the absolute signal size, as noted above, and to accommodate expansion and contraction of the conductor 20 as the subject breathes, the conductor 20 is supported on the substrate 22 in a zigzag pattern.

The use of a zigzag pattern contributes a component of inductance which is a measure of the circumference of the torso (or other encircled body part) rather than changes in the cross-sectional area of the encircled part which are measured by changes in the axial dimension of the conductor 20. Where the inductive plethysmograph 12 encircles the torso, it has been determined that the circumferential inductance component actually decreases as the patient inhales, i.e. as the torso expands, thereby partially cancelling out the increase in inductance resulting from the change in cross-sectional area. Similar to the Q-factor discussed above, the desired cross-sectional area component of inductance measured by the inductive plethysmograph increases in proportion to the square of the number of turns of the conductor 20 about the torso, while the undesired circumferential component increases more slowly in proportion to the number of turns. It will therefore be apparent that in a single-turn inductive plethysmograph 12, the circumferential inductance component will reduce the output signal to a much greater extent then will be the case in a multiple turn inductive plethysmograph. In fact, it has been determined that in a single-turn inductive plethysmograph, the circumferential component reduces the output signal to approximately a third of its potential value (expressed as the percent frequency change for a given percent area change), i.e. the inductance value that would result solely from changes in cross-sectional area.

From the foregoing discussion, it will be apparent that the sensitivity of the inductive plethysmograph 12 increases with an increasing number of turns. Accordingly, any number of wire turns greater than one will improve the sensitivity of the inductive plethysmograph. The upper limit in the number of turns is limited only by practical considerations such as manufacturing ease, production costs, and the number of available pins in the connectors 26, 28. Five turns is presently believed to be an appropriate compromise between such practical considerations and improved sensitivity.

While we have herein shown and described a preferred embodiment of our invention and suggested certain changes and modifications thereto, those of ordinary skill in the art will appreciate that still further changes and modifications may be made therein without departing from the spirit and scope of the invention. Accordingly, the above description should be construed as illustrative and not in a limiting sense, the scope of the invention being defined by the following claims.

We claim:

1. In an apparatus comprising at least one inductive plethysmograph for disposition about a subject and incorporating a conductor, said conductor comprising the inductance component of an LC oscillator circuit, said conductor being electrically connected to said oscillator circuit through an impedance matching transformer with a secondary winding of the transformer being electrically connected to said conductor and a primary winding thereof being electrically connected to said oscillator circuit, the improvement comprising:

said conductor being electrically connected to said transformer via a connecting cable, said connecting cable being sufficiently long that said oscillator circuit and said transformer are disposed sufficiently remote from said plethysmograph to prevent said oscillator circuit and said transformer from contact with said plethysmograph or said subject when said subject is lying on said connecting cable; and said transformer primary winding having an inductance greater than about ten times the reflected inductance of said conductor and said cable, whereby attenuation of changes in the inductance of said conductor and connecting cable is reduced.

2. The apparatus of claim 1, wherein the inductance of the primary winding of said transformer is about ten times the reflected inductance of said conductor and said cable.

3. The apparatus of claim 1, wherein said cable has a length of about ten feet.

4. The apparatus of claim 3, wherein said cable comprises a coaxial cable having a center conductor and a screen, wherein the ratio of a diameter of said screen to a diameter of said center conductor is minimized for reducing the inductance per unit length thereof.

5. The apparatus of claim 4, wherein the inductance per unit length of said cable is less than about 0.1 microhenries per foot.

6. The apparatus of claim 5, wherein the inductance per unit length of said cable is about 0.03 microhenries per foot.

7. The apparatus of claim 1, wherein the turns ratio of said transformer steps up the combined impedance of said inductive plethysmograph and said cable to about 150 ohms.

8. The apparatus of claim 1, wherein said cable comprises a coaxial cable having a center conductor and a screen, wherein the ratio of a diameter of said screen to a diameter of said center conductor is minimized for reducing the inductance per unit length thereof.

9. The apparatus of claim 8, wherein said conductor has a plurality of turns whereby when said inductive plethysmograph is in encircling relation about a body part said conductor encircles said body part a plurality of times for improving the sensitivity of said apparatus.

10. The apparatus of claim 9, wherein said inductive plethysmograph comprises a stretchable substrate and wherein said conductor is arranged in a zigzag pattern on said stretchable substrate.

11. The apparatus of claim 10, wherein said inductive plethysmograph comprises two free ends joinable by mating connectors and further comprises lengths of conductor supported on said substrate with one end of each conductor length being joined to one connector and the other end being joined to the other connector, whereby when said connectors are joined said conductor having a plurality of turns is formed.

12. The apparatus of claim 8, wherein the inductance per unit length of said cable is less than about 0.1 microhenries per foot.

13. The apparatus of claim 12, wherein the inductance per unit length of said cable is about 0.03 microhenries per foot.

14. The apparatus of claim 1, wherein said conductor has a plurality of turns whereby when said inductive plethysmograph is in encircling relation about a body part said conductor encircles said body part a plurality of times for improving the sensitivity of said apparatus.

15. The apparatus of claim 14, wherein said inductive plethysmograph comprises a stretchable substrate and wherein said conductor is arranged in a zigzag pattern on said stretchable substrate.

16. The apparatus of claim 15, wherein said inductive plethysmograph comprises two free ends joinable by mating connectors and further comprises lengths of conductor supported on said substrate with one end of each conductor length being joined to one connector and the other end being joined to the other connector, whereby when said connectors are joined said conductor having a plurality of turns is formed.

17. The apparatus of claim 1, wherein said connecting cable is at least ten feet.

18. In an apparatus of the type comprising at least one inductance plethysmograph adapted for placement in encircling relation about a body portion of a subject, said inductive plethysmograph incorporating a conductor which comprises the inductance component of an LC oscillator circuit, the improvement comprising:
said conductor having a plurality of turns whereby when said inductive plethysmograph is in encircling relation about said body portion said conductor encircles said body portion a plurality of times for improving the sensitivity of said apparatus,
wherein said inductive plethysmograph comprises a stretchable substrate and wherein said conductor is arranged in a zigzag pattern on said stretchable substrate,
wherein said inductive plethysmograph comprises two free ends joinable by mating connectors and further comprises lengths of conductor supported on said substrate with one end of each conductor length being joined to one connector and the other end being joined to the other connector, whereby when said connectors are joined said conductor having a plurality of turns is formed,
wherein said conductor being electrically connected to said oscillator circuit through an impedance matching transformer with a secondary winding of the transformer being electrically connected to said conductor and a primary winding thereof being electrically connected to said oscillator circuit,
wherein said conductor is electrically connected to said transformer via a connecting cable, said connecting cable being sufficiently long that said oscillator circuit and said transformer are disposed sufficiently remote from said plethysmograph to prevent said oscillator circuit and said transformer from contact with said plethysmograph or said subject when said subject is lying on said connecting cable, and
wherein said transformer primary winding having an inductance greater than about ten times the reflected inductance of said conductor and said cable, whereby attenuation of changes int he inductance of said conductor and connecting cable is reduced.

19. The apparatus of claim 18, wherein the inductance of the primary winding of said transformer is about ten times the reflected inductance said conductor and said cable.

20. The apparatus of claim 19, wherein said cable comprises a coaxial cable having a center conductor and a screen, wherein the ratio of a diameter of said screen to a diameter of said center conductor is minimized for reducing the inductance per unit length thereof.

21. The apparatus of claim 20, wherein the inductance per unit length of said cable is less than about 0.1 microhenries per foot.

22. The apparatus of claim 21, wherein the inductance per unit length of said cable is about 0.1 microhenries per foot.

23. The apparatus of claim 18, wherein said cable has a length of about ten feet.

24. The apparatus of claim 18, wherein the turns ratio of said transformer steps up the combined impedance of said inductive plethysmograph and said cable to about 150 ohms.

25. The apparatus of claim 18, wherein said cable comprises a coaxial cable having a center conductor and a screen, wherein the ratio of a diameter of said screen to a diameter of said center conductor is minimized for reducing the inductance per unit length thereof.

26. The apparatus of claim 25, wherein the inductance per unit length of said cable is less than about 0.1 microhenries per foot.

27. The apparatus of claim 26, wherein the inductance per unit length of said cable is about 0.03 microhenries per foot.

28. In an apparatus of the type comprising at least one inductive plethysmograph for disposition about a subject and incorporating a conductor, said conductor comprising the inductance component of an LC oscillator circuit, said conductor being electrically connected to said oscillator circuit through an impedance matching transformer with a secondary winding of the transformer being connected to said conductor and a primary winding thereof being electrically connected to said oscillator circuit, the improvement comprising:
said conductor being electrically connected to said transformer via a connecting cable comprising a coaxial cable comprising a center conductor and a screen, said connecting cable being sufficiently long that said oscillator circuit and said transformer are disposed sufficiently remote from said plethysmograph to prevent said oscillator circuit and said transformer from contact with said plethysmograph or said subject when said subject is lying on said connecting cable, wherein the ratio of a diameter of said screen to a diameter of said center conductor is minimized for reducing the inductance per unit length thereof, and said transformer primary winding having a first number of turns said secondary winding having a second number of turns, a ratio of the first number of turns to the second number of turns is selected so as to compensate for attenuation of changes in inductance of the conductor and the cable.

29. The apparatus of claim 28, wherein the inductance per unit length of said cable is less than about 0.1 microhenries per foot.

30. The apparatus of claim 29, wherein the inductance per unit length of said cable is about 0.03 microhenries per foot.

31. The apparatus of claim 28, wherein said coaxial cable is at least ten feet.

* * * * *